(12) United States Patent
Lodder et al.

(10) Patent No.: US 7,251,032 B2
(45) Date of Patent: Jul. 31, 2007

(54) OPTICAL MONITORING SYSTEM WITH MOLECULAR FILTERS

(75) Inventors: Robert A. Lodder, Nicholasville, KY (US); John Carberry, Talbott, TN (US)

(73) Assignees: Neptec Optical Solutions, Inc., Fremont, CA (US); The University of Kentucky Research Foundation, Lexington, KY (US)

( * ) Notice: Subject to any disclaimer, the term of this patent is extended or adjusted under 35 U.S.C. 154(b) by 124 days.

(21) Appl. No.: 11/185,138

(22) Filed: Jul. 20, 2005
(Under 37 CFR 1.47)

(65) Prior Publication Data

US 2006/0072110 A1 Apr. 6, 2006

Related U.S. Application Data

(60) Provisional application No. 60/589,463, filed on Jul. 20, 2004.

(51) Int. Cl.
*G01N 21/25* (2006.01)
(52) U.S. Cl. .................... 356/414; 356/419
(58) Field of Classification Search ............. 356/414, 356/416, 419
See application file for complete search history.

(56) References Cited

U.S. PATENT DOCUMENTS

| | | | | |
|---|---|---|---|---|
| 3,697,185 | A * | 10/1972 | Kassel et al. .............. 356/410 |
| 4,403,861 | A * | 9/1983 | Boisde et al. .............. 356/407 |
| 4,477,190 | A * | 10/1984 | Liston et al. .............. 356/418 |
| 4,820,045 | A * | 4/1989 | Boisde et al. .............. 356/319 |
| 5,450,194 | A * | 9/1995 | Dureault et al. ............ 356/319 |
| 5,680,220 | A * | 10/1997 | Delignieres et al. ........ 356/406 |
| 6,175,669 | B1 | 1/2001 | Colston et al. |
| 6,191,860 | B1 * | 2/2001 | Klinger et al. .............. 356/419 |
| 6,243,511 | B1 | 6/2001 | Laughlin |
| 6,611,334 | B1 * | 8/2003 | Fernando et al. ............ 356/436 |
| 6,661,512 | B2 * | 12/2003 | Fernando et al. ............ 356/319 |
| 6,735,006 | B2 | 5/2004 | Carberry et al. |
| 6,950,568 | B2 * | 9/2005 | Fernando et al. ............ 385/16 |
| 7,151,869 | B2 * | 12/2006 | Fernando et al. ............ 385/16 |
| 2002/0061159 | A1 | 5/2002 | Dahmani et al. |
| 2004/0252937 | A1 | 12/2004 | Guynn et al. |
| 2005/0225840 | A1 * | 10/2005 | Drasek et al. .............. 359/333 |

* cited by examiner

*Primary Examiner*—Layla G. Lauchman
*Assistant Examiner*—Bryan Giglio
(74) *Attorney, Agent, or Firm*—Alan H. MacPherson; MacPherson Kwok Chen & Heid LLP

(57) ABSTRACT

An optical monitoring system for determining the constituents of a sample or specimen. An absorption spectrum is obtained from a sample and is passed through one or more filters having a specified absorption spectrum defined by a single atom or a compound. If the filter's absorption spectrum is included in the sample's absorption spectrum, then the sample contains that atom or compound. The apparatus includes a switching assembly that sequentially places one or more filters into the light path to determine if the subject atom or compound is contained in the sample.

32 Claims, 3 Drawing Sheets

OPTICAL MONITORING SYSTEM WITH MOLECULAR FILTERS

CROSS-REFERENCE TO RELATED APPLICATIONS

This application claims the benefit of Provisional Application Ser. No. 60/589,463, filed Jul. 20, 2004.

STATEMENT REGARDING FEDERALLY SPONSORED RESEARCH OR DEVELOPMENT

Not Applicable

BACKGROUND OF THE INVENTION

1. Field of Invention

This invention pertains to an optical monitoring system. More particularly, this invention pertains to an optical monitoring system that compares an absorption spectrum of a filter with that obtained from a sample or specimen. The system uses a switching assembly enabling a plurality of filters to be used for the comparison.

2. Description of the Related Art

It is desirable to identify chemical and biological agents and other constituents in fast moving streams or in remote locations where the material to be examined is moving quickly. Examples where such identification is desired include fast moving streams of water, gas and materials, for instance, examining flows of milk for biological agents such as botulism and fast moving streams of water such as in municipal water supplies, where one can identify multiple chemical and biological agents of interest. In all these cases, successful interrogation requires the very quick identification of a number of predetermined constituents.

The sensing of spectral absorption, reflection, transmission and diffraction as a function of wavelengths, bandpass, and other spectral energy measurements allows for identifying both the geometry and composition of materials. Modern hyperspectral imaging (sensing at many wavelengths simultaneously) is able to collect extraordinary amounts of information at amazing speed. However, reducing the data from physical fields of signal values to high-level, useful information is difficult. Integrated computational imaging (ICI) is a process in which image information is encoded as it is sensed to produce information better suited for high-speed digital processing. Both spatial and spectral features of samples can be encoded in ICI. When hyperspectral images are simultaneously obtained and encoded at many different wavelengths, the process is called hyperspectral integrated computational imaging (HICI).

In many cases, it is desirable to inspect and quantify only preselected constituents in areas not easily accessible by ordinary sampling means. Physically extracting a sample can be difficult when exposing the sample to ordinary inspection means such as visual and laboratory analysis because these analyses can destroy the sample. In other cases, such inspection must be done in situ along with other processes.

BRIEF SUMMARY OF THE INVENTION

According to one embodiment of the present invention, an optical monitoring system for determining the constituents of a sample or specimen is provided. An absorption spectrum obtained from a sample, or specimen, is passed through one or more filters having a specified absorption spectrum defined by a single atom, molecule, or compound. If the filter's absorption spectrum is included in the sample's absorption spectrum, then the sample is determined to contain that atom or compound. The apparatus includes a switching assembly that sequentially places one or more filters into the light path to determine if the subject atom or compound is contained in the sample.

In one embodiment, the switching assembly includes a 1×N switch distributing an optical signal to one of several filters with each filter monitored by a photodetector. In another embodiment, the switching assembly includes a first 1×N switch distributing an optical signal to one of several filters. The outputs of the filters are input to a second 1×N switch that switches the signals from the filters to a single photodetector. In still another embodiment, the switching assembly includes a rotary switch that directs the optical signal through one of several filters and into a photodetector. In one such embodiment, the optical signal is directed through a rotating prism, through stationary filters that are located radially around the prism, and into the photodetectors on the opposite side of the filters. In another such embodiment, the optical signal is directed through each of several filters mounted on a rotating disk. The filters rotate around a stationary prism and intercept the optical signal as it travels from the prism to a photodetector.

BRIEF DESCRIPTION OF THE SEVERAL VIEWS OF THE DRAWINGS

The above-mentioned features of the invention will become more clearly understood from the following detailed description of the invention read together with the drawings in which.

DETAILED DESCRIPTION OF THE INVENTION

Figure 1:
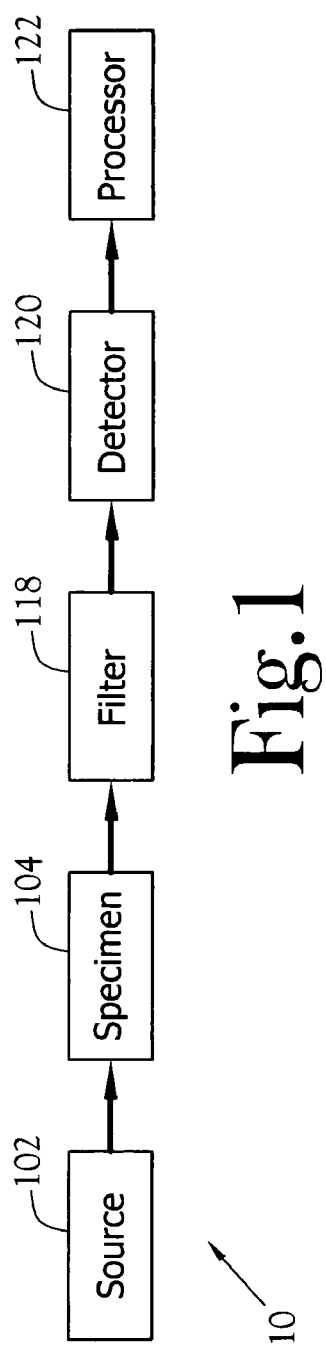
FIG. 1 is a simplified block diagram of one embodiment of the present invention.

FIG. 1 is a simplified block diagram of one embodiment of an optical monitoring system 10, an apparatus for determining the constituents of a sample. A light source 102 is passed through a specimen 104. The light beam, after passing through the specimen 104, passes through a filter 118 and into an optical detector 120. The output of the optical detector 120 is input to a processor 122.

In one embodiment, the light source 102 is a broad-spectrum source, that is, the spectrum is continuous. In one such embodiment, the source 102 includes a tungsten filament. In another embodiment, the light source 102 is either a tunable laser or a laser emitting a continuous spectrum between upper and lower wavelength limits. In still another embodiment, the source 102 includes a broad-spectrum source and a band gap filter, which is an optical filter that selects certain spectra for passage, and rejects others. The light source 102 is then passed through an image field of the specimen 104, which is examined by the light from the source 202 as a function of the specimen's 104 reflection, absorption, transmission, or diffraction within the field.

The specimen 104 absorbs certain wavelengths of the light from the source 102 and produces an absorption spectrum. In an absorption spectrum, portions of a continuous spectrum (light containing all wavelengths) are missing because they have been absorbed by the medium through which the light has passed; the missing wavelengths appear as dark lines or gaps when viewing the absorption spectrum. This is contrasted with an emission spectrum, which consists of all the radiations emitted by atoms or molecules of an incandescent material. The missing portions of an absorption spectrum provide information as to the makeup of the specimen 104 because the missing portions correspond to the constituents of the specimen 104 that absorb the missing wavelengths.

In one embodiment, the filter 118 is a molecular filter, or molecular absorption filter, that is, a filter with such a construction that it produces an absorption spectrum based upon a single atomic element or molecule. From the incoming light source 102 the molecular filter 118 absorbs the spectral lines that correspond to the absorption spectrum of the filter's 118 material. Another characteristic of the filter 118 is the transmittance, that is, the amount of light that is transmitted through the filter 118. Transmittance is typically expressed as a percentage. A lower transmittance results in a greater intensity reduction over the spectrum. That is, a lower transmittance results in a lower light intensity at the output than at the input.

Placing a molecular filter 118 in the light path containing an absorption spectrum from the specimen 104 will have either of two results. If the material producing the absorption spectrum of the filter 118 is contained in the specimen, then there will not be a reduction of the light passing through the filter 118, other than that due to the filter transmittance. The filter 118 does not reduce the light intensity because the absorption spectrum of the filter 118 has all its elements in common with the absorption spectrum of the specimen 104. However, if the material producing the absorption spectrum of the filter 118 is not contained in the specimen, then there will be a reduction of the light passing through the filter 118. The reduction in the intensity of light passing through both the specimen 104 and the filter 118 is due to the filter 118 absorbing wavelengths passed by the specimen 104. In this embodiment, the photodetector 120 is responsive to the wavelengths of interest, that is, the photodetector 120 is sensitive to the light intensity over a wavelength range that encompasses the absorption spectra containing the information used to determine the constituents of the specimen 104.

The sensing and characterizing of spectral absorption, reflection, transmission, and/or diffraction with regard to wavelengths, bandpass gaps, and other spectral energy of various characterizations allows identification of both the geometry and composition of materials within those fields of spectral absorption, reflection, transmission, and/or diffraction.

As used herein, the processor 122 should be broadly construed to mean any computer or component thereof that executes software. The processor 122 includes a memory medium that stores software, a processing unit that executes the software, and input/output (I/O) units for communicating with external devices. Those skilled in the art will recognize that the memory medium associated with the processor 122 can be either internal or external to the processing unit of the processor without departing from the scope and spirit of the present invention.

The processor 122 should be broadly construed to mean any computer or component thereof that executes software. In one embodiment the processor 122 is a general purpose computer, in another embodiment, it is a specialized device for implementing the functions of the invention. Those skilled in the art will recognize that the processor 122 includes an input component, an output component, a storage component, and a processing component. The input component receives input from external devices, such as the optical detector 120. If the external devices, such as the optical detector 120, have an analog device, in one embodiment, the input component includes an analog to digital converter (ADC) for converting the analog input signal to a digital signal used by the processor 122. The output component sends output to external devices, such as a display unit and a printer. The storage component stores data and program code. In one embodiment, the storage component includes random access memory. In another embodiment, the storage component includes non-volatile memory, such as floppy disks, hard disks, and writeable optical disks. The processing component executes the instructions included in the software and routines.

Figure 2:
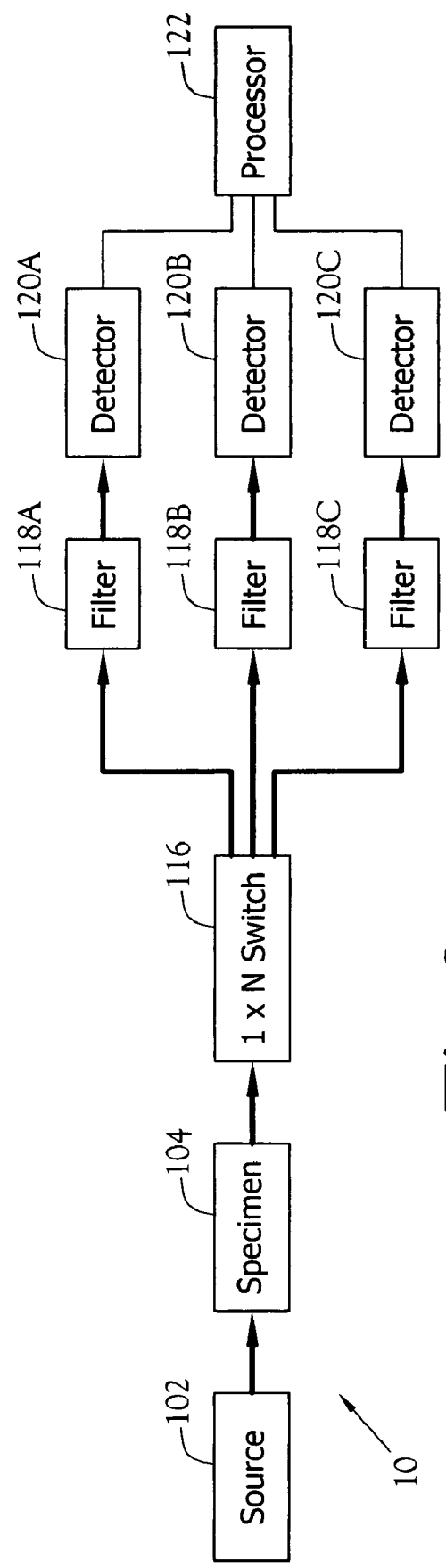
FIG. 2 is a block diagram of another embodiment of the present invention.

FIG. 2 is a block diagram of another embodiment of an optical monitoring system 10'. A light source 102 passes through a specimen 104. The resulting light beam, which is the absorption spectrum of the specimen 104, passes through a 1×N switch 116 that directs the light beam through one of several pairs of filters 118 and detectors 120. By operating the switch 116 to select each of the filters 118A, 118B, 118C sequentially in rapid succession, the specimen 104 is quickly screened for containing one of the materials represented by the molecular filter 118. If the specimen 104 is a flowing or moving material, the illustrated embodiment allows for real-time monitoring and screening of the specimen 104 for specific materials. In such a case, the switching speed of the switch 116 is such that the absorption spectrum from the specimen 104 that is monitored represents a small volume of the ecimen 104, but that volume is monitored with such a frequency that the results that are returned are representative of the real-time concentration of constituents of the specimen 104.

In the illustrated embodiment, the 1×N switch 116 is shown as a 1×3 switch. Those skilled in the art will recognize that the number of ports on the switch 116 must be at least as great as the number of filters 118 desired to be used.

In one embodiment, one of the filters 118A is a neutral density filter that passes the complete spectrum. The output signal of the neutral density filter 118A provides a reference to compare to the output signals of the other filters 118B, 118C. In various other embodiments, one or more filters 118 is a single or cascaded Bragg grating or a thin film filter.

Identification of a number of constituents non-invasively of a specimen 104 is performed by a molecular factor computation system (MFCS) or a principal component analysis (PCA) for each constituent where each MFCS or PCA is quickly switched by an optical switch 116 through and out of an optical fiber, allowing a variety of constituents to be interrogated within a very short period. For each preselected constituent, a molecular factor component (MFC) can be quickly calculated using an optical switch 116, molecular factor filters 118, and single optical fibers, allowing a variety of constituents to be interrogated with a very short duty cycle.

Integrated computational imaging (ICI) is the abstraction of data from physical fields and encoded instream to produce meaningful information. Both spectral and spatial data is recorded and encoded into meaningful information. Further, the use of very wide spectrum or wavelengths, or wide bandgaps, called hyperspectral integrated computational imaging (HICI), provides the basis for using molecular filters 118 for near instant identification of constituents, or materials, pre-selected by the filters 118. Such information, in various embodiments, is a function of transmission, reflectance, diffraction, or absorption of the source 102 by the specimen 104 being interrogated.

Lenslet arrays, masks, filters, and detectors of various types are employed to encode spatial or spectral features of an HICI. Both MFCS and PCA are used to create spectrometer functions that produce factor scores, in the case of MFCS at the detector, which allow, in combination with optical switches, the rapid remote interrogation for a number of factors.

Given a set of training spectra collected at all available wavelengths, it is possible to rationally select molecular filter (MF) materials to perform PCA, which maximizes the signals from the spectral regions with the most variability by most heavily weighting them in calibration. However, principal component loadings heavily weight signals in the positive and negative direction, which cannot be done with molecular filters without offsetting signal gained at one wavelength with signal lost at another wavelength. Because only absolute values are represented with molecular filters, two molecular filters are needed for a principal component, one for the positive loadings and one for the negative loadings. The molecular filter materials are selected by examining the sample spectra. The transmission spectrum of the molecular filter material is as similar as possible to the absolute value of the loadings spectrum being targeted.

Both PCA and MFC are used to create spectrometer functions that produce factor scores. However, only MFC completes PCA at the detector without a computer, which allows, through optical switches, the rapid remote interrogation of a sample for a number of factor scores. The molecules in each molecular filter effectively compute the calibration function by weighting the signals received at each wavelength over a broad wavelength range. Each molecular filter is a correlate for identifying a material of interest, be it a biological agent or a chemical entity.

The MFC computing molecules are selected by comparing the spectrum of prospective molecular filter materials to the loadings spectra calculated by PCA. Given a set of training spectra collected at all available wavelengths or at least those of interest for the molecular filter system being considered, one rationally selects molecular filters materials to perform PCA. Using a conventional spectrometer, mixtures of liquid molecular filters can be titrated to produce the optimum PC result. Digital libraries of the spectra of a variety of candidate filters can be examined in reference to the training spectra by spectral matching software.

Increasing the number of wavelengths in calibration and prediction increases the specificity and produces a model less susceptible to spectral noise if the right wavelengths and weightings are selected. Both PCA and MFC are calibrated to measure constituents of interest while ignoring most interferences, and both are applied to analysis of complex systems because only calibration information on the constituents of interest is necessary and considered.

A molecular factor computation system (MFCS) differs from PCA in that molecular absorption filters provide information relating to the spatial and spectral features of an HICI and are used as mathematical factors in spectral encoding to create a factor analytic optical calibration in a high throughput spectrometer. Also, PCA is slower than MFC, which uses molecular filters that correspond directly to sample constituents. Molecular absorption filters 118 are used as mathematical factors in spectral encoding to create a factor-analytic optical calibration in a high-throughput spectrometer. The molecular filters 118 compute the calibration function by weighting the signals received at each wavelength over a broad wavelength range. One or two molecular filters 118 are oftentimes sufficient to produce a detector voltage that is proportional to an analyte concentration in the image field. Each filter 118 is a correlate for identifying a material of interest, be it a biological agent or a chemical entity.

MFC computing molecules for the molecular filters 118 are selected by comparing the spectrum of prospective filter materials to the loadings spectra calculated by PCA. Given a set of training spectra collected at all available wavelengths, or at least those of interest for the molecular filter system being considered, one rationally selects molecular filter 118 materials to perform PCA. PCA is designed to maximize the signals from the spectral regions with the most variability by most heavily weighting them in calibration. The spectrum of the filter materials should be as similar as possible to the absolute value of the loadings spectrum being targeted. Using a conventional spectrometer, mixtures of liquid molecular filters are titrated to produce the optimum PC result. In one embodiment, digital libraries of the spectra of a wide variety of candidate filters are examined in reference to the training spectra by image recognition software.

Using more wavelengths or a broadband light source provides a good averaging effect that produces a model less susceptible to spectral noise. Both PCA and MFC are calibrated to measure constituents of interest while ignoring most interferences, and both are applied to complex analysis and systems because only calibration information on the constituents of interest is necessary and considered.

Variations in the spectrum from a sample 104 are due to several factors, including the differences in the specimen constituents, interactions between constituents, and overall absorbance. In molecular computing, the molecular filters are selected to maximize the integrated differences in the variation-spectra within a certain bandpass. In PCA, the variation-spectra are used in place of the raw spectral data for constructing the calibration model. The variation spectra are used to reconstruct the original spectrum of a certain sample by multiplying each variation-spectrum by a unique constant scaling factor and summing the results until the new spectrum agrees with the unknown spectrum. The fraction of each spectrum that must be added to reconstruct the unknown spectral data is associated with the concentration of the constituents.

In PCA, the spectra of the variations are termed eigenvectors, or loadings, spectral loadings, loading vectors, or principal components or factors, based on the means used to compute the spectra. Eigenvectors are related to loadings. The scaling factors employed to reconstruct the individual spectra are called scores. Ordinary spectroscopy and PCA chemometrics record signals with a narrow bandpass at each wavelength and weights the signals a at each wavelength $\lambda$ with a coefficient f:

$$\text{score} = f_1 a_{\lambda,1} + f_2 a_{\lambda,2} + f_3 a_{\lambda,3} + f_4 a_{\lambda,4} +$$

It is possible to weight each wavelength in a spectrum optically using the absorbance spectra of filter molecules. The scores are determined by reading a voltage level from a photodetector and integrating the total light through the sample and filter over a broad wavelength band. Although the scores may not be perfectly orthogonal, they are often sufficiently close to permit chemical analysis.

The specific use of MFCS in combination with one or more optical switches 116 uses optical fields for the interrogation and identification of pre-selected chemical and biological agents and constituents. In one embodiment such as illustrated in FIG. 1, MFCS provides a very quick identification of one element or constituent of the specimen 104. In another embodiment, such as illustrated in FIGS. 2 and 3, the use of a switch 116 increases the reliability of each identification, as well as the very quick identification of many pre-selected constituents of the specimen 104.

Figure 3:
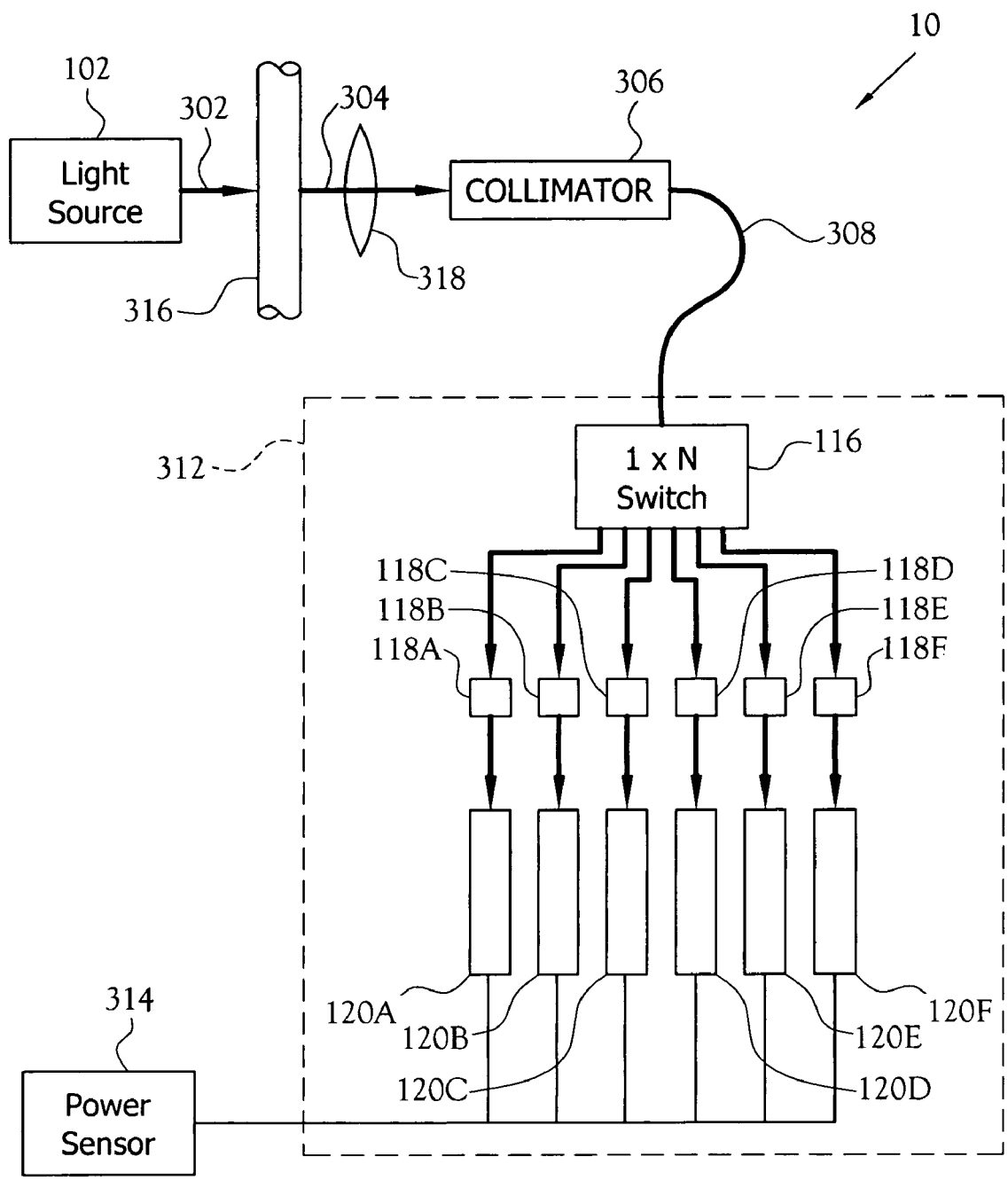
FIG. 3 is a schematic diagram of one embodiment of the present invention.

FIG. 3 is a diagram of one embodiment of the optical monitoring system 10'. The light source 102 directs a light beam 302 though a pipe 316 that contains the specimen 104 to be analyzed. The light beam 304 that has passed through the pipe 316 includes the absorption spectrum of the specimen 104. The light beam 304 is collected and focused by a lens 318 and directed into a collimator 306. A fiber optic cable 308 transports the light beam 304 from the collimator 306 to a switching assembly 312. In the embodiment illustrated, the switching assembly 312 includes a 1×N switch 116 that has a single input from the fiber optic cable 308 and multiple outputs, each one to a filter 118A to F. The light passes through each filter 118A to F into a corresponding photodetector 120A to F. The outputs of the photodetectors 120 are monitored by a power sensor 314 that determines the intensity of the light beam 304 after it passes through the filter 118. In one embodiment, the photodetectors 120 are responsive to the intensity of the light over the wavelength band of interest.

In one embodiment, the power sensor 314 is implemented by software running on the processor 122. In one embodiment, the analog signals from the detectors 120 are converted by an analog to digital converter (ADC). The software reads the input ports and stores the values corresponding to the outputs of the detectors 120. In another embodiment, the detectors 120 include ADCs that output digital signals that are input to the processor 122.

In the illustrated embodiment, the specimen 104 flows through a pipe 316 that is transparent to the wavelengths of the light beam 302. In another embodiment, the specimen 104 is contained in a vessel with a pair of optically transparent windows. In still another embodiment, the specimen 104 is introduced into the light path from the light source 102 at any point between the light source 102 and the detectors 120.

Figure 4:
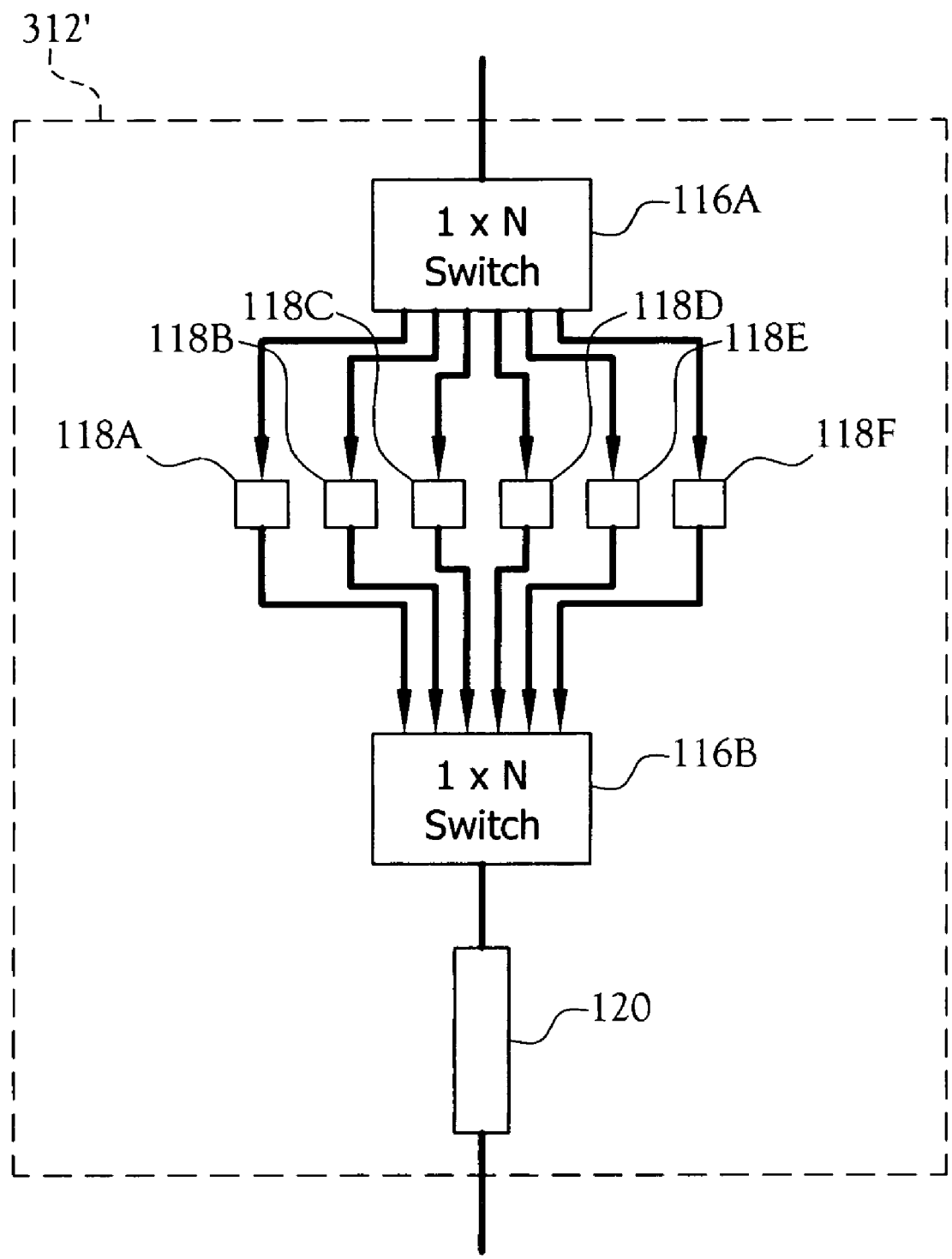
FIG. 4 is a schematic diagram of another embodiment of the switching mechanism.

FIG. 4 is a diagram of another embodiment of the switching assembly 312'. In this embodiment, the first 1×N switch 116A directs the light beam 304 from the specimen 104 to a selected one of the filters 118A to F and the second 1×N switch 116B receives the light beam 304 after it passes through selected one of the filters 118A to F and passes it to a single photodetector 120. In the illustrated embodiment of the switching assembly 312, a single detector 120 is used and the two switches 116A, 116B are synchronized to select the same single filter 118A to F.

In another embodiment, the switching assembly 312' includes a rotary switch that directs the optical signal 304 through one of several filters 118 and into a photodetector 120. In one such embodiment, the optical signal 304 is directed through a rotating prism, through stationary filters 118 that are located radially around the prism, and into the photodetectors 120 on the opposite side of the filters 118. In another such embodiment, the optical signal 304 is directed through each of several filters 118 mounted on a rotating disk. The filters are rotated around a stationary prism and intercept the optical signal 304 as it travels from the prism to a photodetector 120.

In another embodiment of the optical monitoring system 10', the switching assembly 312, 312' includes an optical splitter instead of the switch 116. The optical splitter directs the optical signal 304 to several filters 118. In this embodiment, the light source 102 intensity and the transmission of the specimen 104 must be great enough to overcome the light losses of the optical splitter.

The switching speed of the switching assembly 312, 312' is dependant upon several factors, such as the rate of change of the specimen as it moves through the light beam 302, the rate at which the switch 116 can select each of the filters 118, the number of filters 118, and the response time of the photodetector 120. In one embodiment, the switching assembly 312 has a cycle time of 50 milliseconds, that is, the switch 116 changes state in 50 ms, which is substantially greater than the response time of a typical photodetector 120. High speed photodetectors are readily obtainable with response times on the order of 5 nanoseconds or less. In one embodiment, the switching assembly 312 includes a rotary switch that operates at 120,000 RPM. Such a rotary switch with one revolution not having any filters 118 duplicated has a sampling rate of 2000 samples per second. If the rotary switch includes duplicate filters 118, the sampling rate increases based on the number of duplicate filters 118. For example, a rotary switch with 21 filters 118 arranged as three sets of seven filters 118 has a sampling rate of 6000 samples per second with the switch rotating at 120,000 RPM.

The specimen 104, in various embodiments, is a liquid or gas through which a light beam 302 is capable of passing. In one embodiment, the specimen 104 is milk and the filters 118 are selected to detect impurities and/or contaminates in the milk. Because of the opacity of milk, the pipe 316 or other fluid chamber is selected to minimize the distance the light beam 302 must travel through the milk, thereby ensuring that the light beam 304 with the milk's absorption spectrum has the greatest possible intensity. In another embodiment, the specimen 104 is water, such as that from a municipal water supply. In this embodiment, water is less opaque then milk, and, accordingly, the light beam 302 can travel through a greater volume than with milk. Anti-terrorism assessments have concluded that there should be concern and monitoring of municipal water supplies for approximately two dozen chemical and biological agents.

In another embodiment, the light source 102, conditioned by a bandpass filter, is directed rapidly by an optical switch or optical array through a number of optically correct tubes or passages and a molecular filter 118 into a photodiode 120. Each of these tubes carries a specimen 104 as a stream of liquid or gas and is examined by a specific molecular filter 118 for a pre-selected candidate or constituent. In this embodiment, for example, if light is switched rapidly through a switch 116 or array and the stream of water or gas is divided among the multiple passages, the examination occurs rapidly.

The optical monitoring system 10, 10' includes various functions. The function of switching a light beam with an absorption spectrum from the specimen to one or more filters is implemented, in one embodiment, by a 1×N optical switch 116. In one such embodiment, the optical switch 116 is a rotary switch.

The function of determining an intensity of the light beam passing through the at least one filter is implemented, in one embodiment, by the detector 120. In one embodiment, a single detector 120 is in optical communication with a N×1 optical switch 116B that has its inputs in optical communication with a plurality of filters 118. In another embodiment, each filter 118 is in optical communication with a detector 120.

The function of determining if the constituent represented by the molecular filter is contained in the specimen is implemented, in one embodiment, by the power sensor 314 in communication with the at least one photodetector 120. In various embodiments, the function of the power sensor 314 is implemented by hardware, software, or both, operating together.

From the foregoing description, it will be recognized by those skilled in the art that an optical monitoring system 10, 10' has been provided. The optical monitoring system 10', in one embodiment, passes a light beam 302 from a light source 102 through a specimen 104 and into a switching assembly 312. The switching assembly 312, 312' includes means for directing a light beam through multiple filters 118 and into one or more photodetectors 120. When the filters 118 are molecular filters having an absorption spectrum corresponding to a compound or material of interest, the presence of that compound or material can be determined.

While the present invention has been illustrated by description of several embodiments and while the illustrative embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicant's general inventive concept.

We claim:

1. An optical monitoring system for determining at least one constituent of a specimen, said apparatus comprising:
   - an optical switch receiving a light beam with an absorption spectrum from the specimen and having a plurality of outputs;
   - a first filter in optical communication with a first one of said plurality of outputs of said optical switch, said first filter having a first filter output, said first filter being a molecular filter representing a first constituent and having a first filter transmittance;
   - a first photodetector in optical communication with said first filter output, said first photodetector responsive to said light beam when switched to said first filter and having a first photodetector output indicating a first filter intensity of said light beam,
   - a second filter in optical communication with a second one of said plurality of outputs of said optical switch, said second filter having a second filter output, said second filter being a neutral density filter having a second filter transmittance equal to said first filter transmittance;
   - a second photodetector in optical communication with said second filter output, said second photodetector responsive to said light beam when switched to said second filter and having a second photodetector output indicating a reference intensity of said light beam; and
   - a power sensor in communication with said first photodetector output and said second photodetector output, said power sensor responsive to an intensity of said light beam whereby said first filter intensity is compared to said reference intensity to determine if the specimen contains said constituent.

2. The optical monitoring system of claim 1 further including a light source directed at the specimen and producing said light beam.

3. The optical monitoring system of claim 1 further including a light source directed at the specimen and producing said light beam, said light source being a broadband light source.

4. The optical monitoring system of claim 1 wherein said optical switch is a rotary optical switch, said rotary optical switch having a rotating prism for redirecting said light beam from an axis of rotation to said first and second filters positioned radially around said rotating prism.

5. The optical monitoring system of claim 1 further including a third filter selected from a group including a single Bragg grating, a cascaded Bragg grating, and a thin film filter, said third filter in optical communication with said optical switch.

6. The optical monitoring system of claim 5 further including a third photodetector in optical communication with an output of said third filter.

7. An optical monitoring system for determining at least one constituent of a specimen, said apparatus comprising:
   - a first optical switch receiving a light beam with an absorption spectrum from the specimen and having a plurality of outputs;
   - a first filter in optical communication with a first one of said plurality of outputs of said optical switch, said first filter having a first filter output, said first filter being a molecular filter representing a first constituent and having a first filter transmittance;
   - a second filter in optical communication with a second one of said plurality of outputs of said optical switch, said second filter having a second filter output, said second filter being a neutral density filter having a second filter transmittance equal to said first filter transmittance;
   - a second optical switch having a plurality of inputs and an output, said second optical switch in optical communication with said first filter output and said second filter output; and
   - a photodetector in optical communication with said output of said second optical switch, said second optical switch adapted to operate in tandem with said first optical switch such that said photodetector is responsive to said light beam.

8. The optical monitoring system of claim 7 further including a light source directed at the specimen and producing said light beam.

9. The optical monitoring system of claim 7 further including a light source directed at the specimen and producing said light beam, said light source being a broadband light source.

10. The optical monitoring system of claim 7 further including a power sensor in communication with an output of said photodetector.

11. The optical monitoring system of claim 7 further including a power sensor in communication with an output of said photodetector, said power sensor responsive to an intensity of said light beam.

12. The optical monitoring system of claim 7 wherein said first optical switch is a rotary optical switch, said rotary optical switch having a rotating prism for redirecting said light beam from an axis of rotation to said first and second filters positioned radially around said rotating prism.

13. The optical monitoring system of claim 7 further including a third filter selected from a group including a single Bragg grating, a cascaded Bragg grating, and a thin film filter, said third filter in optical communication with said first and second optical switches.

14. An optical monitoring system for determining at least one constituent of a specimen, said apparatus comprising:
   - a first optical switch receiving a light beam with an absorption spectrum from the specimen and having a plurality of outputs;

at least one filter in optical communication with at least one of said plurality of outputs of said optical switch, said at least one filter having an output, a second optical switch having a plurality of inputs and an output, said second optical switch in optical communication with said at least one filter; and a photodetector in optical communication with said output of said second optical switch, said second optical switch adapted to operate in tandem with said first optical switch such that said photodetector is responsive to said light beam.

15. The optical monitoring system of claim 14 wherein said at least one filter includes a molecular filter representing a first constituent and having a molecular filter transmittance.

16. The optical monitoring system of claim 14 wherein said at least one filter includes a neutral density filter having a neutral density filter transmittance.

17. The optical monitoring system of claim 14 wherein said at least one filter includes a molecular filter representing a first constituent and having a molecular filter transmittance, said at least one filter also includes a neutral density filter having a neutral density filter transmittance.

18. The optical monitoring system of claim 14 further including a power sensor in communication with an output of said photodetector, said at least one filter including a molecular filter representing a first constituent and having a molecular filter transmittance, said at least one filter also including a neutral density filter having a neutral density filter transmittance, said power sensor responsive to an intensity of said light beam switched through said molecular filter and said neutral density filter whereby an intensity of said light beam passed through said molecular filter is compared to an intensity of said light beam passed through said neutral density filter.

19. The optical monitoring system of claim 14 further including a power sensor in communication with an output of said photodetector.

20. The optical monitoring system of claim 14 further including a power sensor in communication with an output of said photodetector, said power sensor responsive to an intensity of said light beam.

21. The optical monitoring system of claim 14 further including a light source directed at the specimen and producing said light beam.

22. The optical monitoring system of claim 14 further including a light source directed at the specimen and producing said light beam, said light source being a broadband light source.

23. The optical monitoring system of claim 14 wherein said first optical switch is a rotary optical switch, said rotary optical switch having a rotating prism for redirecting said light beam from an axis of rotation to said first and second filters positioned radially around said rotating prism.

24. The optical monitoring system of claim 14 wherein said at least one filter includes a filter selected from a group including a molecular filter, a neutral density filter, a single Bragg grating, a cascaded Bragg grating, and a thin film filter.

25. An optical monitoring system for determining at least one constituent of a specimen, said apparatus comprising:

an optical switch receiving a light beam with an absorption spectrum from the specimen and having a plurality of outputs;

a first filter in optical communication with a first one of said plurality of outputs of said optical switch, said first filter having a first filter output, said first filter being a molecular filter representing a first constituent and having a first filter transmittance;

a first photodetector in optical communication with said first filter output, said first photodetector responsive to said light beam when switched to said first filter and having a first photodetector output indicating a first filter intensity of said light beam; and a power sensor in communication with said first photodetector output.

26. The optical monitoring system of claim 25 further including:

a second filter in optical communication with a second one of said plurality of outputs of said optical switch, said second filter having a second filter output, said second filter being a neutral density filter having a second filter transmittance equal to said first filter transmittance; and a second photodetector in optical communication with said second filter output, said second photodetector responsive to said light beam when switched to said second filter and having a second photodetector output indicating a reference intensity of said light beam, said power sensor in communication with said second photodetector output whereby said first filter intensity is compared to said reference intensity to determine if the specimen contains said constituent.

27. The optical monitoring system of claim 25 further including a light source directed at the specimen and producing said light beam.

28. The optical monitoring system of claim 25 further including a light source directed at the specimen and producing said light beam, said light source being a broadband light source.

29. The optical monitoring system of claim 25 wherein said optical switch is a rotary optical switch, said rotary optical switch having a rotating prism for redirecting said light beam from an axis of rotation to said first and second filters positioned radially around said rotating prism.

30. The optical monitoring system of claim 25 further including a third filter selected from a group including a single Bragg grating, a cascaded Bragg grating, and a thin film filter, said third filter in optical communication with said optical switch.

31. An optical monitoring system for determining at least one constituent of a specimen, said apparatus comprising:

at least one molecular filter representing a first constituent;

a means for switching a light beam with an absorption spectrum from the specimen to said at least one molecular filter; and a means for determining an intensity of said light beam passing through said at least one molecular filter.

32. The optical monitoring system of claim 31 further including means for determining if said constituent is contained in the specimen.

* * * * *